US008946490B2

(12) United States Patent
Mirk et al.

(10) Patent No.: US 8,946,490 B2
(45) Date of Patent: Feb. 3, 2015

(54) PROCESS FOR PRODUCING FATTY ALCOHOLS BY HYDROGENATION OF FATTY ACID TRIGLYCERIDES ON A COPPER-CONTAINING HETEROGENEOUS CATALYST

(75) Inventors: Daniela Mirk, Haβloch (DE); Roman Prochazka, Mannheim (DE); Jochem Henkelmann, Mannheim (DE); Markus Hölzle, Kirchheim (DE); Daniela Herzberg, Sion (CH)

(73) Assignee: BASF SE, Ludwigshafen (DE)

( * ) Notice: Subject to any disclaimer, the term of this patent is extended or adjusted under 35 U.S.C. 154(b) by 120 days.

(21) Appl. No.: 13/319,830

(22) PCT Filed: May 19, 2010

(86) PCT No.: PCT/EP2010/056859
§ 371 (c)(1),
(2), (4) Date: Nov. 30, 2011

(87) PCT Pub. No.: WO2010/133619
PCT Pub. Date: Nov. 25, 2010

(65) Prior Publication Data
US 2012/0083631 A1  Apr. 5, 2012

(30) Foreign Application Priority Data
May 20, 2009  (EP) .................................. 09160709

(51) Int. Cl.
C07C 27/04 (2006.01)
C07C 29/149 (2006.01)
C07C 29/17 (2006.01)

(52) U.S. Cl.
CPC ............. *C07C 29/149* (2013.01); *C07C 29/177* (2013.01)
USPC ...................................................... 568/885

(58) Field of Classification Search
USPC ...................................................... 568/885
See application file for complete search history.

(56) References Cited

U.S. PATENT DOCUMENTS

| | | | |
|---|---|---|---|
| 4,297,247 A | 10/1981 | Krabetz et al. | |
| 4,626,604 A | 12/1986 | Hiles et al. | |
| 4,942,266 A | 7/1990 | Fleckenstein et al. | |
| 4,954,664 A | 9/1990 | Carduck et al. | |
| 4,982,020 A | 1/1991 | Carduck et al. | |
| 5,233,100 A * | 8/1993 | Tabata et al. .................. | 568/885 |
| 5,364,986 A | 11/1994 | Demmering et al. | |
| 5,399,792 A | 3/1995 | Demmering | |
| 5,475,160 A | 12/1995 | Singleton et al. | |
| 5,677,261 A | 10/1997 | Tenten et al. | |
| 2004/0133049 A1 | 7/2004 | Pelzer et al. | |
| 2006/0178539 A1 | 8/2006 | Huber-Dirr et al. | |
| 2008/0299390 A1 | 12/2008 | Houssin et al. | |
| 2010/0240934 A1 | 9/2010 | Henkelmann et al. | |
| 2010/0312023 A1 | 12/2010 | Henkelmann et al. | |
| 2010/0312024 A1 | 12/2010 | Henkelmann et al. | |
| 2011/0036012 A1 | 2/2011 | Hatscher et al. | |
| 2011/0251439 A1 | 10/2011 | Mirk et al. | |
| 2011/0268652 A1 | 11/2011 | Machhammer et al. | |
| 2011/0282107 A1 | 11/2011 | Maurer et al. | |
| 2012/0022179 A1 | 1/2012 | Emge et al. | |

FOREIGN PATENT DOCUMENTS

| | | |
|---|---|---|
| DE | 1154448 B | 9/1963 |
| DE | 29 09 671 A1 | 10/1980 |
| DE | 3708430 A1 | 9/1988 |
| DE | 4129622 A1 | 3/1993 |
| DE | 4242466 A1 | 6/1994 |
| DE | 19843798 A1 | 3/2000 |
| DE | 10313702 A1 | 10/2004 |
| EP | 0063427 A2 | 10/1982 |
| EP | 0254189 A2 | 1/1988 |
| EP | 714 700 A2 | 6/1996 |
| WO | WO-96/14280  * | 5/1996 |
| WO | WO-9614280 A1 | 5/1996 |
| WO | WO-1996014280  * | 5/1996 |
| WO | WO-0143873 A2 | 6/2001 |
| WO | WO-2006/005505 A1 | 1/2006 |
| WO | WO-2007/099161 A1 | 9/2007 |
| WO | WO-2009027500 A2 | 3/2009 |
| WO | WO-2009027501 A2 | 3/2009 |
| WO | WO-2009027502 A2 | 3/2009 |
| WO | WO-2010121899 A1 | 10/2010 |

OTHER PUBLICATIONS

English translation of International Preliminary Report on Patentability of PCT/EP2010/056859 mailed Nov. 28, 2011.
International Search Report for PCT/EP2010/056859 mailed Jul. 22, 2010.
International Preliminary Report on Patentability for PCT/EP2010/056859 mailed Aug. 18, 2011.
U.S. Appl. No. 13/265,412, filed 2011, Henkelmann, et al.
International Preliminary Report on Patentability for PCT/EP2010/056859, (2011).
English translation of Japanese Office Action report in Japanese Application No. 511272/2012 dated Jul. 1, 2014.

* cited by examiner

*Primary Examiner* — Yong Chu
*Assistant Examiner* — Sonya Wright
(74) *Attorney, Agent, or Firm* — Drinker Biddle & Reath LLP

(57) ABSTRACT

The present invention relates to a process for preparing fatty alcohols, in which a stream comprising at least one fatty acid triglyceride is provided and this stream is subjected to a hydrogenation in the presence of a heterogeneous copper catalyst.

15 Claims, No Drawings

PROCESS FOR PRODUCING FATTY ALCOHOLS BY HYDROGENATION OF FATTY ACID TRIGLYCERIDES ON A COPPER-CONTAINING HETEROGENEOUS CATALYST

CROSS-REFERENCE TO RELATED APPLICATIONS

This application is a national stage application (under 35 U.S.C. §371) of PCT/EP2010/056859, filed May. 19, 2010, which claims benefit of European application 09160709.3, filed May. 20, 2009.

BACKGROUND OF THE INVENTION

The present invention relates to a process for preparing fatty alcohols, in which a stream comprising at least one fatty acid triglyceride is provided and this stream is subjected to a hydrogenation in the presence of a heterogeneous copper catalyst.

Fatty alcohols are important intermediates for a multitude of chemical products, for example surfactants and cosmetic products. They can be prepared, for example, by hydrogenating fatty acid methyl esters, which are obtainable from fatty or oily starting materials by transesterifying the triglycerides present. A further product of value obtained is glycerol, which can be subjected, for example, to a hydrogenation to obtain 1,2-propanediol.

It is known that the hydrogenation of glycerol to prepare 1,2-propanediol can be performed in the presence of heterogeneous copper catalysts. Such processes are described, for example, in WO 2007/099161, WO 2009/027500, WO 2009/027501 and WO 2009/027502.

It is also known that fatty alcohols can be prepared by direct hydrogenation of triglyceride-containing starting materials, for example of natural oils and fats.

DE-B 1 154 448 describes a process for preparing relatively high molecular weight mono- and polyhydric alcohols by catalytic hydrogenation of fats, fatty acids and fatty acid esters using tableted copper-zinc, copper-chromium, copper-manganese, copper-zinc-chromium, copper-manganese-chromium, copper-cadmium, copper-cadmium-chromium and copper-cadmium-manganese catalysts.

EP 0 063 427 A2 describes a process for selective hydrogenation of unsaturated fatty acid derivatives in the presence of ammonia and a catalyst which comprises at least one metal selected from Pd, Pt, Ir and Rh.

EP 0 254 189 A2 describes a process for direct hydrogenation of glyceride oils in the presence of catalysts which comprise 30 to 40% by weight of copper, 23 to 30% by weight of chromium, 1 to 7% by weight of barium, based in each case on oxidic catalyst material, and if desired further transition metals in the form of oxides thereof.

DE 37 08 430 A1 describes a process for direct hydrogenation of butterfat in the presence of catalysts which comprise 30 to 40% by weight of copper, 23 to 30% by weight of chromium, 1 to 10% by weight of manganese, 1 to 10% by weight of silicon and 1 to 7% by weight of barium, based in each case on oxidic catalyst material, and if desired further transition metals in the form of oxides thereof.

DE 41 29 622 A1 describes a process for preparing unsaturated fatty alcohols by hydrogenation over a zinc-chromium catalyst of the spinel type.

DE 198 43 798 A1 describes a process for preparing fatty alcohols by hydrogenating fatty acids or fatty acid esters over a fixed catalyst bed, in which unconverted hydrogen is recovered and recycled into the hydrogenation and the reactor is cooled by sparging with unheated hydrogen.

WO 01/43873 A2 describes oxidic zinc-aluminum catalysts for the preparation of unsaturated fatty alcohols by hydrogenating unsaturated fatty acids, fatty acid lower alkyl esters or fatty acid glycerides.

US 2004/0133049 A1 describes a process for preparing fatty alcohols from fatty acids, fatty acid esters and naturally occurring triglycerides in a fixed bed reactor. Suitable hydrogenation catalysts described include oxidic copper-aluminum catalysts.

WO 96/14280 describes a process for directly hydrogenating carboxylic acids to fatty alcohols in the presence of a catalyst which comprises a copper compound, a zinc compound and at least one compound selected from compounds of aluminum, zirconium, magnesium, rare earth metals and mixtures thereof.

BRIEF SUMMARY OF THE INVENTION

DE 42 42 466 A1 describes a process for preparing fatty alcohols, in which natural fats and oils are hydrogenated in the presence of optionally calcined copper-zinc catalysts at a high hydrogen pressure and high temperature in a continuous tube bundle reactor.

It is an object of the present invention to provide an improved process for preparing fatty alcohols. Thus, the known processes are still in need of improvement with regard to substantially complete hydrogenation of the fatty acid triglycerides with simultaneously good selectivity for 1,2-propanediol as a further product of value. The process provided should especially be suitable both for processing fatty acid triglyceride streams from biogenic sources and fatty acid triglyceride streams obtained in industry.

It has now been found that, surprisingly, heterogeneous copper catalysts where the catalytically active component of the catalyst additionally comprises aluminum and at least one further metal selected from lanthanum, tungsten, molybdenum, titanium, zirconium and mixtures thereof are particularly advantageously suitable for one-stage hydrogenation of fatty acid triglyceride streams to obtain fatty alcohols. They especially enable substantially complete one-stage hydrogenation. Advantageously, these catalysts are also notable for a high selectivity with respect to 1,2-propanediol as a further product of value of the hydrogenation.

The invention therefore provides a process for preparing fatty alcohols, in which
a) a stream comprising at least one fatty acid triglyceride is provided,
b) the stream comprising fatty acid triglyceride is subjected to a hydrogenation in the presence of a heterogeneous copper catalyst, the catalytically active component of the catalyst additionally comprising aluminum and at least one further metal selected from lanthanum, tungsten, molybdenum, titanium, zirconium and mixtures thereof,
c) at least one fatty alcohol-containing fraction is isolated from the hydrogenation product obtained in step b).

A DETAILED DESCRIPTION OF THE INVENTION

In the context of the invention, the term "fatty alcohol" denotes saturated and unsaturated alcohols having 6 to 40, preferably 8 to 30, especially 10 to 28, carbon atoms. The fatty alcohols are especially linear alcohols.

In a specific embodiment, the fatty alcohols are saturated fatty alcohols or fatty alcohol mixtures which comprise predominantly saturated fatty alcohols (i.e. to an extent of at least 80%).

The process according to the invention enables a one-stage (i.e. direct) hydrogenation of a starting material containing fatty acid triglycerides to a product containing fatty alcohols. "One-stage" is understood to mean that the fatty acid triglyceride-containing starting material is used for hydrogenation without preceding transesterification of the fatty acid triglycerides, for example to fatty acid methyl esters. The process according to the invention also enables the hydrogenation of a fatty acid triglyceride-containing starting material without preceding conversion to increase the content of free fatty acids. The hydrogenation in the process according to the invention can, however, be effected in at least two hydrogenation reactors connected in series. In this configuration, however, the isolation of partly hydrogenated intermediates is generally dispensed with.

Step a)

For provision of the fatty acid triglyceride-containing stream, all available biogenic oily and/or fatty starting mixtures are suitable in principle. Oils and fats are generally solid, semisolid or liquid fatty acid triglycerides, especially from vegetable and animal sources, which consist in chemical terms essentially of glyceryl esters of higher fatty acids. Suitable higher fatty acids are saturated or mono- or polyunsaturated fatty acids having preferably 6 to 40, more preferably 8 to 30, especially 10 to 28, carbon atoms. Examples include n-nonanoic acid, n-decanoic acid, n-undecanoic acid, n-tridecanoic acid, myristic acid, pentadecanoic acid, palmitic acid, margaric acid, nonadecanoic acid, arachic acid, behenic acid, lignoceric acid, cerotic acid, melissic acid, palmitoleic acid, oleic acid, linoleic acid, linolenic acid, stearic acid, eleostearic acid, etc.

Vegetable fats and oils are based essentially on fatty acids with an even number of carbon atoms, whereas animal fats and oils may also comprise fatty acids with an odd number of carbon atoms in bound form as triglyceride esters. The unsaturated fatty acids which occur in vegetable fats and oils are present in the cis form, whereas animal fatty acids frequently have trans configuration.

To provide the fatty acid triglyceride-containing stream in step a), it is possible in principle to use used or unused, unpurified or purified, vegetable, animal or industrial oils or fats or mixtures thereof. They may comprise proportions of further ingredients, for example free fatty acids. The proportion of free fatty acids is generally 0% to 20%, for example 0.1 to 15%, based on the total weight of the fatty acid triglyceride-containing stream provided in step a).

To provide the fatty acid triglyceride-containing stream in step a), it is possible if desired to partly or completely remove free fatty acids. Salts of these fatty acids (for example the alkali metal salts) can be converted to the free acid beforehand by acidifying with a strong acid, for example HCl. It is possible to remove the free fatty acids, for example, by centrifugation.

Unused fats and oils suitable for providing the fatty acid triglyceride-containing stream in step a) are fatty or oily components which, after they have been obtained from the corresponding vegetable or animal starting materials, have yet to be sent to any other use and therefore comprise only ingredients which originate from the starting materials or are connected to the extraction from the starting materials. It is possible, if desired, to at least partly remove ingredients other than fatty acid triglycerides (and, optionally, free fatty acids) from these starting materials, before the use for hydrogenation in step b).

Used fats and oils suitable for providing the fatty acid triglyceride-containing stream in step a) are fatty and/or oily components which, after they have been obtained from corresponding biogenic starting materials, have first been used for other purposes, for example for industrial purposes, or purposes of food production, and which are chemically modified owing to this use or unmodified, or may comprise additional ingredients which are especially connected to this use. These may, if desired, be removed at least partly for providing the fatty acid triglyceride-containing stream.

For purification and/or enrichment, the unused or used fats or oils can be subjected to a removal of undesired constituents, such as lecithins, carbohydrates, proteins, oil sludge, water, etc.

Vegetable oils and fats are those which originate predominantly from vegetable starting materials, such as seeds, roots, leaves or other suitable plant parts. Animal fats or oils originate predominantly from animal starting materials, such as animal organs, tissues or other body parts, or body fluids such as milk. Industrial oils and fats are those which have been obtained especially from animal or vegetable starting materials and have been processed for industrial purposes. The used or unused, unpurified or purified oils and/or fats used in accordance with the invention are especially selected from the group consisting of soapstock, brown grease, yellow grease, industrial tallow, industrial lard, deep fat fryer oils, animal fat, edible tallow, crude vegetable oils, crude animal oils or fats, or mixtures thereof.

"Soapstock" is understood to mean a by-product obtained in the processing of vegetable oils, especially a by-product of cooking oil refineries, based on soybean oil, colza oil or sunflower oil. Soapstock has a proportion of free fatty acids of about 50% to 80%.

"Brown grease" is understood to mean an animal fat-containing waste product which has a proportion of free fatty acids of more than 15% to 40%. "Yellow grease" contains about 5% to 15% free fatty acids.

"Industrial tallow" and "industrial lard" are understood to mean animal fats which are produced for industrial purposes and are obtained by the dry or wet melting process, for example, from slaughter wastes. Industrial tallows are rated and treated according to their acid number, the content of free fatty acids, according to the origin, being, for example, between 1 and 20% by weight, for example in the range from 1 to 15% by weight. The content of free fatty acids may, however, also be more than 20% by weight.

The "animal fats" include especially fatty waste products in the processing of poultry, cattle, pig, fish and marine mammal bodies, for example solar stearin, a solid residue which remains after the extractive pressing of lard oil from pork lard.

The fatty acid triglyceride-containing stream is preferably provided in step a) from crude vegetable oils as the starting material. It is possible to proceed from unpurified crude vegetable oils, i.e. from liquid or solid compositions obtained from vegetable starting materials, for example by pressing, in which case they have undergone no other treatment than settling within generally customary periods and spinning or filtration, in which only mechanical forces such as gravity, centrifugal force or pressure are used to separate the oil from solid constituents. Such unpurified crude vegetable oils may also be vegetable oils obtained by extraction when their properties differ only insignificantly, if at all, from the corresponding vegetable oils obtained by means of pressing. The proportion of free fatty acids in unpurified vegetable fats and oils is different and is, for example, about 0 to 20%, for example 0.1 to 15%.

It will be appreciated that the vegetable oils, before they are used for hydrogenation in step b), may be subjected to one or more processing steps, as described in more detail hereinafter. For instance, it is also possible to use purified vegetable oils, for example raffinates or semiraffinates, of the aforementioned vegetable oils as starting materials.

Preference is given to using, for provision of the fatty acid triglyceride-containing stream in step a), a vegetable oil or fat which is preferably selected from rapeseed oil, palm oil, colza oil, soybean oil, sunflower oil, maize kernel oil, cottonseed oil, palm kernel fat and coconut fat and mixtures thereof. Particular preference is given to using rapeseed oil or a rapeseed oil-containing mixture.

Also suitable for provision of the fatty acid triglyceride-containing stream in step a) is animal oil or fat, which is preferably selected from milk fat, wool fat, bovine tallow, pork lard, fish oils, train oil, etc., and mixtures thereof.

The fatty acid triglyceride-containing stream provided in step a) preferably has a water content of at most 30% by weight, preferably of at most 20% by weight. In a specific embodiment, in step a) a fatty acid triglyceride-containing stream which is essentially anhydrous is provided. In the context of the present invention, "essentially anhydrous" is understood to mean a water content of at most 3% by weight, more preferably of at most 1% by weight. The use of fatty acid triglyceride-containing streams having a water content in the range up to 30% by weight, especially up to 20% by weight, enables the preparation of fatty alcohols and 1,2-propanediol with high yields and with high selectivity within the temperature and pressure ranges used for the hydrogenation in step b).

The fatty acid triglyceride-containing streams may, instead of or in addition to water, comprise at least one organic solvent. The fatty acid triglyceride-containing streams provided in step a) preferably have a total solvent content of at most 20% by weight, more preferably at most 15% by weight, more particularly at most 10% by weight and especially at most 5% by weight. When solvent mixtures which comprise water and at least one water-miscible organic solvent are used, the proportion of the organic solvent is preferably at most 50% by weight, more preferably at most 20% by weight, based on the total weight of the solvent. Preferred organic solvents are $C_1$-$C_4$ alkanols, such as methanol, ethanol, n-propanol, isopropanol, n-butanol, tert-butanol, polyols and mono- and dialkyl ethers thereof, cyclic ethers, such as dioxane and tetrahydrofuran, etc. Suitable solvents are also aromatic hydrocarbons such as benzene, toluene, or the xylenes. Preferred organic solvents are $C_1$-$C_4$ alkanols, especially methanol and/or ethanol and mixtures thereof with water. However, the fatty acid triglyceride-containing streams provided in step a) and used for hydrogenation in step b) preferably do not comprise any organic solvent.

The fatty acid triglyceride-containing streams provided in step a) may be subjected to at least one workup step. This includes, for example, at least one purification step for removing undesired components. This also includes a reduction in the content of water and/or, if present, of organic solvent.

In a specific embodiment, the provision of the fatty acid triglyceride-containing stream in step a) comprises at least one purification step. To this end, a fatty and/or oily starting mixture can be subjected to at least one customarily used purification process for fats and oils, such as clarifying, filtration, treatment with bleaching earths or treatment with acids or alkali to remove troublesome impurities such as proteins, phosphatides and slimy substances, or else a combination of at least two of these purification steps.

According to the origin, the fatty acid triglyceride-containing streams may still comprise inorganic salts as an undesired component. These can be removed by known workup processes. A suitable process for this purpose is especially a thermal workup (for example using a Sambay evaporator).

According to the origin, the fatty acid triglyceride-containing streams may also comprise catalyst poisons, i.e. components which impair the hydrogenation by deactivating the hydrogenation catalyst. These include, for example, nitrogen compounds such as amines, and sulfur compounds such as sulfuric acid, hydrogen sulfide, thioalcohols, thioethers, e.g. dimethyl sulfide and dimethyl disulfide, carbon oxide sulfide, amino acids, e.g. amino acids comprising sulfur groups and additional nitrogen groups, fatty acids and salts thereof, etc. The catalyst poisons also include halogen compounds, traces of customary extractants, for example, acetonitrile or N-methylpyrrolidone, etc., and optionally organic phosphorus and arsenic compounds.

For the workup of the fatty acid triglyceride-containing streams provided in step a), it is possible, for example, to use a thermal workup, preferably a distillation, an adsorption, an ion exchange, a membrane separation process, a crystallization, an extraction or a combination of two or more of these processes. Membrane separation processes using membranes of defined pore sizes are suitable especially for reducing the water content and/or for removing salt. Crystallization is also understood to mean the partial freezing of the fatty acid triglyceride-containing streams at cooled surfaces. It is thus possible to remove impurities which accumulate in the solid phase.

In a first embodiment, the fatty acid triglyceride-containing stream provided in step a) is subjected to a distillation to reduce the water content and/or to remove components which impair the catalytic hydrogenation. This can in principle be done by customary distillation processes known to those skilled in the art. Suitable apparatus for distillative workup comprises distillation columns, such as tray columns which may be equipped with bubble-caps, sieve plates, sieve trays, structured packings, random packings, valves, side draws, etc., evaporators such as thin-film evaporators, falling-film evaporators, forced-circulation evaporators, Sambay evaporators, etc., and combinations thereof.

Suitable separation processes are described in the documents which follow: Sattler, Klaus: Thermische Trennverfahren [Thermal Separation Processes], 3rd edition, Wiley VCH, 2001; Schlünder E. U., Thurner F.: Destillation, Absorption, Extraktion [Distillation, Absorption, Extraction], Springer Verlag, 1995; Mersmann, Alfons: Thermische Verfahrenstechnik [Thermal Process Technology], Springer Verlag, 1980; Grassmann P., Widmer F.: Einführung in die thermische Verfahrenstechnik [Introduction to Thermal Process Technology], de Gruyter, 1997; Weiss S., Militzer K.-E., Gramlich K.: Thermische Verfahrenstechnik, Dt. Verlag für Grundstoffindustrie, Leipzig, Stuttgart, 1993. Reference is made here to these documents.

In a further embodiment, the fatty acid triglyceride-containing stream provided in step a) is subjected to a catalytic desulfurization, optionally in the presence of hydrogen, to reduce the content of sulfur compounds, especially aromatic sulfur compounds. Suitable desulfurizing agents comprise a metal component, the metal preferably being selected from the metals of groups 6, 7, 8, 9, 10, 11 and 12 of the Periodic Table. The metals are preferably selected from Mo, Ni, Cu, Ag, Zn and combinations thereof. Suitable further components of the desulfurizing agents are dopants. The metal component may be used in oxidic form, reduced form or in the form of a mixture which comprises oxidized and reduced components. The active component of the desulfurizing agents (metal component(s) and optionally dopant(s)) may be applied to a support. Suitable supports are in principle the adsorbents and catalyst supports specified below. The support material is preferably selected from activated carbon, graphite, carbon black, $Al_2O_3$, $SiO_2$, $TiO_2$, $ZrO_2$, SiC, silicates, zeolites, aluminas (e.g. bentonites) and combinations thereof. The application of at least one metal component and optionally of further components to a support material can be effected by known processes, for example by (co)precipitation or impregnation. The desulfurizing agents may be used as shaped bodies, for example, in the form of pressed cylinders, tablets, pellets, wagonwheels, rings, stars or extrudates, such as solid extrudates, polylobal extrudates, hollow extrudates and honeycombs, or other geometric bodies. Unsupported desulfurizing agents can be shaped by customary processes, for example by extrusion, tableting, etc. The shape of supported desulfurizing agents is determined by the shape of the support.

For the catalytic desulfurization, preference is given to using a desulfurizing agent which comprises copper and zinc in an atomic ratio of 1:0.3 to 1:10, preferably 1:0.5 to 1:3, especially 1:0.7 to 1:1.5. Preference is given to using a desulfurizing agent which comprises 35 to 45% by weight of copper oxide, 35 to 45% by weight of zinc oxide and 10 to 30% by weight of aluminum oxide. In a specific embodiment, the desulfurizing agent is a component capable of being used as a hydrogenation catalyst in step b). In this regard, reference is made to the disclosure which follows regarding hydrogenation catalysts and processes for their preparation.

In one configuration of this process variant, the fatty acid triglyceride-containing streams are contacted with the desulfurizing agent in at least one desulfurization zone and then hydrogenated in at least one reaction zone.

It is obvious to the person skilled in the art that the specific configuration and arrangement of the desulfurization and reaction zone(s) can be effected in any known manner. It is possible to arrange the desulfurization and reaction zone(s) spatially separately from one another, i.e. to separate them from one another in construction terms by virtue of the apparatus arrangement or else to realize them in one or more combined desulfurization/hydrogenation zone(s).

The copper-zinc desulfurizing agent can be obtained, for example, by a customary precipitation or coprecipitation process and be used in oxidized or in reduced form.

In a particular embodiment, the copper-zinc desulfurizing agent comprises at least copper, zinc and aluminum, in which case the copper:zinc aluminum atomic ratio is in the range from 1:0.3:0.05 to 1:10:2, preferably 1:0.6:0.3 to 1:3:1 and especially 1:0.7:0.5 to 1:1.5:0.9.

For conversion to the reduced form it is possible to subject the desulfurizing agent to a hydrogen reduction. This is performed at about 150 to 350° C., preferably at about 150 to 250° C., in the presence of hydrogen, in which case the hydrogen is diluted by an inert gas, for example nitrogen, argon, methane, especially nitrogen, such that the hydrogen content is 10% by volume or less, preferably 6% by volume or less, especially 0.5 to 4% by volume. The copper-zinc desulfurizing agent thus obtained ("reduced form") may be used in this form in the desulfurization.

In one embodiment, the desulfurization of the fatty acid triglyceride-containing stream is performed over the copper-zinc desulfurizing agent in oxidized form without addition of hydrogen.

In a further embodiment, the desulfurization of the fatty acid triglyceride-containing stream is performed over the copper-zinc desulfurizing agent in oxidized form in the presence of hydrogen.

In a further embodiment, the desulfurization of the fatty acid triglyceride-containing stream is performed over the copper-zinc desulfurizing agent in reduced form without addition of hydrogen.

In a further embodiment, the desulfurization of the fatty acid triglyceride-containing stream is performed over the copper-zinc desulfurizing agent in reduced form in the presence of hydrogen.

Typically, the desulfurization is performed within a temperature range from 40 to 200° C., particularly at 50 to 180° C., especially at 60 to 160° C., preferably at 70 to 120° C., at a pressure of 1 to 40 bar, particularly at 1 to 32 bar, preferably at 1.5 to 5 bar, especially at 2.0 to 4.5 bar. The desulfurization can be performed in the presence of inert gases, for example nitrogen, argon or methane. In general, however, the desulfurization is performed without addition of inert gases.

Typically—if desired—hydrogen is used herewith a purity of ≥99.8% by volume, especially of ≥99.9% by volume, preferably of ≥99.95% by volume. These purities apply analogously to the hydrogen, which is used in the optionally performed activations of the catalysts.

Typically, the weight ratio of fatty acid triglyceride-containing stream to hydrogen is in the range from 40 000:1 to 1000:1, particularly in the range from 38 000:1 to 5000:1, more particularly in the range from 37 000:1 to 15 000:1, preferably in the range from 36 000:1 to 25 000:1, especially in the range from 35 000:1 to 30 000:1.

The fatty acid triglyceride-containing stream thus desulfurized generally has a content of sulfur impurities, especially of aromatic sulfur compounds, of at most 70 ppb, preferably of at most 50 ppb, and the total sulfur content is a total of ≤200 ppb, preferably ≤150 ppb, especially ≤100 ppb.

The above-described desulfurizing agents also enable the reduction in the level of or the removal of chlorine, arsenic and/or phosphorus or corresponding chlorine, arsenic and/or phosphorus compounds from the fatty acid triglyceride-containing stream.

In a further embodiment, the fatty acid triglyceride-containing stream provided in step a) is contacted with at least one adsorbent to remove components which impair the catalytic hydrogenation.

The adsorbents preferably have a specific surface area, determined according to BET, in the range from 10 to 2000 $m^2/g$, more preferably in the range from 10 to 1500 $m^2/g$, more particularly in the range from 10 to 400 $m^2/g$, especially in the range from 60 to 250 $m^2/g$.

Suitable adsorbents are, for example, active aluminum oxides. They are prepared, for example, proceeding from aluminum hydroxide, which is obtainable by customary precipitation processes from aluminum salt solutions. Active aluminum oxides suitable for the process according to the invention are also obtainable proceeding from aluminum hydroxide gels. To prepare such gels, it is possible, for example, to activate precipitated aluminum hydroxide by customary workup steps, such as filtering, washing and drying, and then optionally to grind or agglomerate it. If desired, the resulting aluminum oxide can then also be subjected to a shaping process, such as extrusion, granulation, tableting, etc. Suitable adsorbents are preferably the Selexsorb™ types from Alcoa.

Suitable adsorbents are also aluminum oxide-containing solids. These include, for example, the aluminas which likewise comprise aluminum oxides as the main constituent.

Additionally suitable adsorbents are aluminum phosphates.

Further suitable adsorbents are silicon dioxides, which are obtainable, for example, by dewatering and activating silica gels. A further process for preparing silicon dioxide is the flame hydrolysis of silicon tetrachloride, in which suitable variations of the reaction parameters, for example of the stoichiometric composition of the reactant mixture and of the temperature, allow the desired surface properties of the resulting silicon dioxide to be varied within wide ranges.

Further suitable adsorbents are kieselguhrs, which likewise have silicon dioxides as the main constituent. These include, for example, the diatomaceous earths obtained from silica sediments.

Further suitable adsorbents are titanium dioxides and zirconium dioxides, as described, for example, in Römpp, Chemie-Lexikon, 9th ed. (paperback), vol. 6, p. 4629 ff. and p. 5156 ff. and the literature cited there. This is fully incorporated here by reference.

Further suitable adsorbents are phosphates, especially condensed phosphates, for example, fused or calcined phosphates which have a large active surface area. Suitable phosphates are described, for example, in Römpp, Chemie-Lexikon, 9th ed. (paperback), vol. 4, p. 3376 ff. and the literature cited there. This is fully incorporated here by reference.

Further suitable adsorbents are carbon-containing adsorbents, preferably activated carbon. Activated carbon is understood here generally to mean carbon with a porous structure and high internal surface area. To prepare activated carbon, vegetable, animal and/or mineral carbon-containing raw materials are heated, for example, with dehydrating agents, such as zinc chloride or phosphoric acid, or carbonized by dry distillation and then activated oxidatively. For this purpose, the carbonized material can, for example, be treated with steam, carbon dioxide, and/or mixtures thereof at elevated temperatures of about 700 to 1000° C.

It is also possible to use ion exchangers and/or adsorber resins.

The adsorbents are preferably selected from titanium dioxides, zirconium dioxides, silicon dioxides, kieselguhr, aluminum oxides, aluminum oxide-containing solids, aluminum phosphates, natural and synthetic aluminum silicates, phosphates, carbon-containing adsorbents and mixtures thereof.

The adsorbents generally have a specific surface area, determined according to BET, in the range from about 10 to 2000 $m^2/g$, more particularly in the range from 10 to 1500 $m^2/g$ and especially in the range from 20 to 600 $m^2/g$.

For the adsorptive removal of undesired components, more particularly of components which impair the catalytic hydrogenation, the fatty acid triglyceride-containing stream provided in step a) is contacted with at least one adsorbent in an adsorption zone.

In a specific embodiment, an adsorbent which comprises at least one component also capable of being used as a hydrogenation catalyst in step b) is used. Full reference is made here to the hydrogenation catalysts described in more detail below. Also suitable for use as adsorbents are combinations of two or more than two adsorbents. It is possible to use exclusively components capable as hydrogenation catalysts, exclusively adsorbents not suitable as hydrogenation catalysts, and combinations thereof.

In a preferred embodiment, the adsorbent and the hydrogenation catalyst used are the same component. Optionally, one or more further conventional adsorbents other than the hydrogenation catalyst, as described above, are additionally used here.

In one configuration of the process, the fatty acid triglyceride-containing streams are contacted with the adsorbent in at least one adsorption zone and then hydrogenated in at least one reaction zone.

It is obvious to the person skilled in the art that the specific configuration and arrangement of the adsorption and reaction zone(s) can be effected in any known manner. Preference is given to arranging the adsorption and reaction zone(s) spatially separately from one another, i.e. to separating them from one another in construction terms by virtue of the apparatus configuration.

When different adsorbents are used, it is possible, for example, to provide a first adsorption zone in a first reactor which comprises a first adsorbent, and separately, i.e. separately therefrom in apparatus terms, for example in a second reactor, to provide a second adsorption zone which comprises a second adsorbent. In this case, the first and/or the second adsorbent may comprise at least one component capable of being used as a hydrogenation catalyst.

In a further embodiment, a conventional adsorbent is used together with an adsorbent capable of hydrogenation in a single adsorption zone, for example in layered form one on top of another, mixed in the form of a random distribution or in the form of a gradient bed. The use in mixed form allows, optionally, better control of the temperature. In the case of a gradient bed, it is possible to use linear and nonlinear gradients. It may be advantageous here to undertake the distribution within the bed such that the fatty acid triglyceride-containing stream to be hydrogenated is first contacted with the conventional adsorbent before it is contacted with the adsorbent capable of hydrogenation.

Advantageously, at least two adsorption zones will be arranged such that the fatty acid triglyceride-containing stream to be hydrogenated is contacted with a conventional adsorbent in the first adsorption zone, and is contacted with an adsorbent which comprises at least one component capable of being used as a hydrogenation catalyst in the second adsorption zone.

Step b)

According to the invention, for the hydrogenation in step b), a heterogeneous catalyst which comprises copper, aluminum and at least one further metal selected from lanthanum, tungsten, molybdenum, titanium, zirconium and mixtures thereof is used.

The heterogeneous hydrogenation catalysts used in the process according to the invention may be unsupported catalysts or supported catalysts. They may be used in the form of catalysts of homogeneous composition, impregnated catalysts, coated catalysts and precipitation catalysts.

Suitable catalysts may comprise the metals in oxidic form, reduced form (elemental form) or a combination thereof. Metals which are stable in more than one oxidation state may be used completely in one of the oxidation states or in different oxidation states.

A specific embodiment of catalysts which are particularly advantageously suitable for use in the process according to the invention is that of catalysts which comprise copper in oxidic form and optionally additionally in elemental form. The hydrogenation catalyst used in step b) then preferably comprises at least 25% by weight, more preferably at least 35% by weight, of copper in oxidic and/or elemental form, based on the total weight of the catalyst.

Particularly preferred catalysts comprise the following metals: Cu, Al, La or Cu, Al, W.

A frequently employed process for preparing such catalysts consists in the impregnation of support materials with solutions of the catalyst components, which are subsequently converted to the catalytically active state by thermal treatment, decomposition or reduction.

A further suitable process for preparing catalysts comprises the precipitation of at least one catalyst component. Various catalyst components can be precipitated in succession or two or more than two catalyst components can be precipitated in a coprecipitation. For instance, to prepare a shaped catalyst body, a copper compound, at least one further metal compound and optionally at least one additive can be precipitated and then subjected to drying, calcination and shaping. The precipitation can be carried out in the presence of a support material. Suitable starting materials for the precipitation are metal salts and metal complexes. The metal compounds used for the precipitation may in principle be all known metal salts which are soluble in the solvents used for the application to the support. These include, for example, nitrates, carbonates, acetates, oxalates or ammonium complexes. In a preferred embodiment, at least one metal nitrate is used. For the precipitation, preference is given to an aqueous medium.

Suitable aqueous media are substances or mixtures which are liquid under the process conditions and which comprise at least 10% by weight, more preferably at least 30% by weight and especially at least 50% by weight of water. The proportion other than water is preferably selected from inorganic or organic compounds which are at least partly soluble in water or at least partly miscible with water. For example, the compounds other than water are selected from organic solvents, such as $C_1$-$C_{20}$ alkanols, especially methanol, ethanol, n-propanol, isopropanol, n-butanol, sec-butanol, tert-butanol, pentanols and hexanols, $C_4$-$C_8$-cycloalkyl ethers such as tetrahydrofurans, pyrans, dioxanes and trioxanes, $C_1$-$C_{12}$-dialkyl ethers such as dimethyl ether, dibutyl ether and methyl butyl ether. The aqueous medium comprises preferably less than 40% by weight, more preferably less than 30% by weight and especially less than 20% by weight of organic solvents. In a preferred embodiment of the process according to the invention, the aqueous medium is essentially free of organic solvents.

The precipitation can be induced by known processes, for example cooling of a saturated solution, addition of a precipitant, etc. Suitable precipitants are, for example, acids, bases, reducing agents, etc.

The precipitation can be induced by adding an acid or a base to the aqueous medium which comprises the copper compound and optionally further compounds. Suitable acids are mineral acids such as HCl, $H_2SO_4$ and $H_3PO_4$. The base is preferably selected from metal oxides, metal hydroxides, especially alkali metal hydroxides such as sodium hydroxide and potassium hydroxide, metal carbonates, especially alkali metal and alkaline earth metal carbonates such as lithium carbonate, sodium carbonate, potassium carbonate, magnesium carbonate and calcium carbonate, nitrogen bases, especially ammonia and primary, secondary and tertiary amines.

Examples of suitable reducing agents are carboxylic acids such as formic acid, citric acid, lactic acid, tartaric acid and especially salts of carboxylic acids, preferably the alkali metal, alkaline earth metal, ammonium and $C_1$-$C_{10}$-alkylammonium salts, phosphorous or hypophosphorous acid, the salts of phosphorous or hypophosphorous acid, especially the alkali metal or alkaline earth metal salts, $C_1$-$C_{10}$ alkanols such as methanol, ethanol and isopropanol, sugars such as aldoses and ketoses in the form of monosaccharides, disaccharides and oligosaccharides, especially glucose, fructose and lactose, aldehydes such as formaldehyde, boron-hydrogen compounds such as borohydrides, boranes, metal boronates and borane complexes, such as diborane, sodium borohydride and aminoboranes, especially trimethylaminoborane, hydrazine and alkylhydrazines such as methylhydrazine, hydrogendithionites and dithionites, especially sodium and potassium hydrogendithionite, sodium, potassium and zinc dithionites, hydrogensulfides and sulfides, especially sodium and potassium hydrogensulfides, sodium, potassium and calcium sulfides, hydroxylamine and urea, and mixtures thereof.

WO 2006/005505 describes shaped catalyst bodies which are particularly suitable for use in the process according to the invention. These may be prepared by a process in which
(i) an oxidic material comprising copper oxide, aluminum oxide and at least one of the oxides of lanthanum, tungsten, molybdenum, titanium or zirconium, with preference being given to the oxides of lanthanum and/or tungsten, is made available,
(ii) pulverulent metallic copper, copper flakes, pulverulent cement or mixtures thereof or a mixture thereof with graphite can be added to the oxidic material, and
(iii) the mixture resulting from (ii) is shaped to form a catalyst pellet or a catalyst extrudate having a diameter d and/or a height h of <6.0 mm, catalyst spheres having a diameter d of <6.0 mm or catalyst honeycombs having a cell diameter rz of <6.0 mm.

Among the oxides of lanthanum, tungsten, molybdenum, titanium or zirconium, lanthanum oxide is preferred. The composition of the oxidic material is generally such that the proportion of copper oxide is in the range from 40 to 90% by weight, the proportion of oxides of lanthanum, tungsten, molybdenum, titanium or zirconium is in the range from 1 to 59% by weight and the proportion of aluminum oxide is in the range from 1 to 59% by weight, in each case based on the total weight of the sum of the abovementioned oxidic constituents, with these three oxides together making up at least 80% by weight of the oxidic material after calcination and cement not being included as part of the oxidic material in the above sense.

In a preferred embodiment, the oxidic material comprises
(a) copper oxide in a proportion in the range $50 \leq x \leq 80\%$ by weight, preferably $55 \leq x \leq 75\%$ by weight,
(b) aluminum oxide in a proportion in the range $15 \leq y \leq 35\%$ by weight, preferably $20 \leq y \leq 30\%$ by weight, and
(c) at least one of the oxides of lanthanum, tungsten, molybdenum, titanium or zirconium, preferably of lanthanum and/or tungsten, in a proportion in the range $2 \leq x \leq 20\%$ by weight, preferably $3 \leq x \leq 15\%$ by weight,
in each case based on the total weight of the oxidic material after calcination, where $80 \leq x+y+z \leq 100$, in particular $95 \leq x+y+z \leq 100$.

The hydrogenation catalyst used in step b) is preferably a catalyst which comprises an oxidic material of the composition $(CuO)_{0.6-0.8} (Al_2O_3)_{0.1-0.34} (La_2O_3)_{0.02-0.2}$ or consists of such an oxidic material. A specific suitable catalyst has the chemical composition 57% CuO, 28.5% $Al_2O_3$, 9.5% $La_2O_3$ and 5% Cu.

The inert support materials used for the inventive catalysts may be virtually any prior art support materials as used advantageously in the preparation of supported catalysts, for example, $SiO_2$ (quartz), porcelain, magnesium oxide, tin dioxide, silicon carbide, $TiO_2$ (rutile, anatase), $Al_2O_3$ (alumina), aluminum silicate, steatite (magnesium silicate), zirconium silicate, cerium silicate or mixtures of these support materials. Preferred support materials are aluminum oxide and silicon dioxide. The silicon dioxide support material used for catalyst preparation may be silicon dioxide materials of different origin and preparation, for example, fumed silicas, or silicas prepared by wet chemical means, such as silica gels, aerogels, or precipitated silicas (for preparation of the different SiO$_2$ starting materials see: W. Büchner; R. Schliebs; G. Winter; K. H. Büchel: Industrielle Anorganische Chemie [Industrial Inorganic Chemistry]; 2nd ed., p. 532-533, VCH Verlagsgesellschaft, Weinheim 1986).

The catalysts may be used as shaped bodies, for example in the form of spheres, rings, cylinders, cubes, cuboids or other geometric bodies. Unsupported catalysts can be shaped by customary processes, for example by extrusion, tableting, etc. The shape of supported catalysts is determined by the shape of the support. Alternatively, the support can be subjected to a shaping process before or after the application of the catalytically active component(s). The catalysts may, for example, be used in the form of pressed cylinders, tablets, pellets, wagonwheels, rings, stars or extrudates, such as solid extrudates, polylobal extrudates, hollow extrudates and honeycombs or other geometric bodies.

The catalyst particles generally have a mean of the (greatest) diameter of 0.5 to 20 mm, preferably 1 to 10 mm. This includes, for example, catalysts in the form of tablets, for example with a diameter of 1 to 7 mm, preferably 2 to 6 mm, and a height of 3 to 5 mm, rings with, for example, external diameter 4 to 7 mm, preferably 5 to 7 mm, height 2 to 5 mm and hole diameter 2 to 3 mm, or extrudates of different length of diameter of, for example, 1.0 to 5 mm. Such shapes can be obtained in a manner known per se by tableting or extrusion. To this end, customary assistants, for example lubricants such as graphite, polyethylene oxide, cellulose or fatty acids (such as stearic acid), and/or shaping assistants and reinforcers such as fibers of glass, asbestos or silicon carbide, may be added to the catalyst composition.

A specific embodiment of supported catalysts is that of coated catalysts. Coated catalysts comprise a catalytic composition applied in coating form to a support. They may be present in the form of spheres, rings, cylinders, cubes, cuboids, or other geometric bodies. Irrespective of the type and composition of the catalytically active material, coated catalyst particles can in principle be provided by contacting the support with a liquid binder and the catalytically active composition, applying a layer of the composition to the support and then, optionally, partly removing the binder. To provide the catalyst particles, the catalytically active material is applied actually in its finished catalytically active form, for example as a calcined mixed oxide. Suitable processes for preparing coated catalysts are described, for example, in DE-A-29 09 671 and in EP-A-714 700. According to the latter process, the support is first moistened with the liquid binder, then a layer of active catalyst composition is adhered on the surface of the moistened support body by contacting with dry, finely divided, active catalyst composition, and then the liquid binder is partly removed optionally. In a specific embodiment, the steps of moistening the support, of contacting with the catalyst composition and of removing the liquid binder are repeated once or more than once until the desired layer thickness of the coated catalyst has been attained.

A further specific embodiment of supported catalysts is that of catalysts prepared by impregnation processes. To this end, the catalytically active catalyst components or precursor compounds thereof can be applied to the support material. In general, the support material is impregnated by applying aqueous salt solutions of the components, for example, aqueous solutions of their halides, sulfates, nitrates, etc. The copper component may, for example, also be applied to the support material in the form of an aqueous solution of its amine complex salts, for example as a [Cu(NH$_3$)$_4$]SO$_4$ or as a [Cu(NH$_3$)$_4$](NO$_3$)$_2$ solution, optionally in the presence of sodium carbonate. It will be appreciated that it is also possible to use copper-amine complexes other than those mentioned by way of example for the catalyst preparation with the same success.

The support material in principle can be impregnated with the precursor compounds of the catalytically active components in one or more stages. The impregnation can be undertaken in conventional impregnation apparatus, for example impregnating drums. After drying and/or calcination, the finished catalyst is then obtained. The impregnated shaped catalyst bodies can be dried continuously or batchwise, for example in a belt or tray oven. The drying can be effected at atmospheric pressure or reduced pressure. In addition, the drying can be effected in a gas stream, for example, an air stream or a nitrogen stream. According to the pressure employed, the drying is performed generally at temperatures of 50 to 200° C., preferably 80 to 150° C. The catalyst which has optionally been dried beforehand is calcined generally at temperatures of 200 to 800° C., preferably 500 to 700° C. The calcination can, like the drying, be performed continuously or batchwise, for example, in a belt or tray oven. The calcination can be effected under atmospheric pressure or reduced pressure and/or in a gas stream, for example in an air stream or a hydrogen stream. A pretreatment with hydrogen or hydrogen-comprising gases, generally under conditions which correspond to the hydrogenation conditions, serves to pre-reduce/activate the hydrogenation catalyst. The catalyst may, though, also be reduced in situ under the conditions established in the hydrogenation, preferably under pressure (for example at a hydrogen pressure of about 100 to 325 bar).

The hydrogenation in step b) is effected preferably at a temperature within a range from 100 to 320° C., more preferably from 150 to 270° C., especially from 180 to 230° C.

The hydrogenation in step b) is effected preferably at a pressure in the range from 100 to 325 bar, more preferably from 150 to 300 bar, especially from 180 to 230 bar.

The molar ratio of hydrogen to fatty acid triglyceride is preferably 10:1 to 1000:1, more preferably 12.5:1 to 500:1.

The catalyst hourly space velocity in continuous mode is preferably 0.1 to 1 kg, more preferably 0.2 to 0.5 kg, of fatty acid triglyceride to be hydrogenated/kg (catalyst)×h.

The conversion, based on fatty acid triglyceride, is preferably at least 90%, especially at least 95%.

The selectivity in the hydrogenation in step b) for 1,2-propanediol (based on the sum of glycerol and hydrogenation products of glycerol) in the process according to the invention is preferably at least 85%, more preferably at least 90%. In many cases, even higher selectivities of up to 95% and higher can be achieved.

The hydrogenation is preferably performed continuously. The hydrogenation discharge consists essentially of fatty alcohols and 1,2-propanediol. Further constituents are selected from methanol, ethanol, n-propanol, isopropanol, 1,3-propanediol, glycerol, ethylene glycol and water.

In a specific embodiment of the process according to the invention, the hydrogenation is effected in n hydrogenation reactors connected in series, where n is an integer of at least 2. Suitable values of n are 2, 3, 4, 5, 6, 7, 8, 9 and 10. n is preferably 3 to 6 and especially 2 or 3. In this embodiment, the hydrogenation is preferably continuous.

The reactors used for hydrogenation in step b) may each independently have one or more reaction zones within the reactor. The reactors may be identical or different reactors. These may, for example, in each case have identical or different mixing characteristics and/or be divided once or more than once by internals.

Suitable pressure-resistant reactors for the hydrogenation are known to those skilled in the art. These include the generally customary reactors for gas-liquid reactions, for example tubular reactors, tube bundle reactors, gas circulation reactors, bubble columns, loop apparatus, stirred tanks (which may also be configured as stirred tank cascades), airlift reactors, etc.

The process according to the invention using heterogeneous catalysts can be performed in fixed bed or suspension mode. The fixed bed method can be performed, for example, in liquid phase mode or in trickle mode. The catalysts are preferably used as shaped bodies as described above, for example, in the form of pressed cylinders, tablets, pellets, wagonwheels, rings, stars or extrudates such as solid extrudates, polylobal extrudates, hollow extrudates, honeycombs, etc.

In suspension mode, heterogeneous catalysts are likewise used. The heterogeneous catalysts are usually used in a finely distributed state and are present finely suspended in the reaction medium.

Suitable heterogeneous catalysts and processes for their preparation are those described above.

In the case of hydrogenation over a fixed bed, a reactor is used, in whose interior is arranged a fixed bed through which the reaction medium flows. The fixed bed can be formed from a single bed or from a plurality of beds. Each bed may have one or more zones, at least one of the zones comprising a material active as a hydrogenation catalyst. Each zone may have one or more different catalytically active materials and/or one or more different inert materials. Different zones may each have identical or different compositions. It is also possible to provide a plurality of catalytically active zones which are separated from one another, for example, by inert beds. The individual zones may also have different catalytic activities. To this end, different catalytically active materials can be used and/or an inert material can be added to at least one of the zones. The reaction medium which flows through the fixed bed, in accordance with the invention, comprises at least one liquid phase. The reaction medium may also additionally comprise a gaseous phase.

The reactors used in the hydrogenation in suspension are especially loop apparatus such as jet loops or propeller loops, stirred tanks which may also be configured as stirred tank cascades, bubble columns or airlift reactors.

Preference is given to effecting the continuous hydrogenation in step b) in at least two fixed bed reactors connected in series. The reactors are preferably operated in cocurrent. The feed streams can be fed in either from the top or from the bottom.

Under the reaction conditions of the hydrogenation, the fatty acid triglyceride, the resulting fatty alcohols and the resulting 1,2-propanediol are preferably present in the liquid phase. The conditions may be selected such that individual components of the reaction mixture alone would be solid under these conditions. This is the case, for example, for the fatty alcohol(s).

The temperature in the hydrogenation in step b) in all reactors is generally about 150 to 300° C., especially 180 to 250° C.

If desired, in a hydrogenation apparatus composed of n reactors, at least 2 of the reactors (i.e. from 2 to n of the reactors) may have a temperature different from one another. In a specific embodiment, each next reactor downstream is operated with a higher temperature than the upstream reactor. In addition, each of the reactors may have two or more reaction zones with different temperature. For example, a different temperature, preferably a higher temperature, can be established in a second reaction zone than in the first reaction zone, or a higher temperature than in an upstream reaction zone can be established in each downstream reaction zone, for example, in order to achieve substantially full conversion in the hydrogenation.

The reaction pressure in step b) is preferably, in all reactors, generally about 150 to 300 bar, more preferably 180 to 250 bar.

If desired, in the case of a hydrogenation apparatus composed of n reactors, at least 2 of the reactors (i.e. from 2 to n of the reactors) may have a different pressure. In a specific embodiment, each reactor connected downstream is operated with a higher pressure than the upstream reactor.

The hydrogen required for the hydrogenation can be fed into the first and optionally additionally into at least one further reactor. Preference is given to feeding hydrogen only into the first reactor. The amount of hydrogen fed to the reactors arises from the amount of hydrogen consumed in the hydrogenation reaction and the amount of hydrogen optionally discharged with the offgas.

The fatty acid triglyceride content converted in the particular reactor can be adjusted, for example, via the reactor volume and/or the residence time in the reactor. The conversion in the first reactor, based on fatty acid triglyceride, is preferably at least 60%, more preferably at least 70%. The total conversion in step b), based on the fatty acid triglyceride, is preferably at least 97%, more preferably at least 98%, especially at least 99%.

To remove the heat of reaction which arises in the exothermic hydrogenation, it is possible to provide one or more of the reactors with at least one cooling apparatus. In a specific embodiment, at least the first reactor is provided with a cooling apparatus. The heat of reaction can be removed by cooling an external circulation stream or by internal cooling in at least one of the reactors. For the internal cooling, it is possible to use the apparatus customary therefor, generally hollow modules such as Field tubes, tube coils, heat exchanger plates, etc. Alternatively, the reaction can also be effected in a cooled tube bundle reactor.

The hydrogenation in step b) is preferably effected in n hydrogenation reactors connected in series, where n is an integer of at least two, and wherein at least one reactor has a stream from the reaction zone conducted in an external circulation system (external circulation stream, liquid circulation system, loop mode). n is preferably two or three.

The hydrogenation in step b) is preferably effected in n hydrogenation reactors connected in series, where n is preferably two or three, and the 1st to (n−1)th reactor has a stream from the reaction zone conducted in an external circulation system.

The hydrogenation in step b) is preferably effected in n hydrogenation reactors connected in series, where n is preferably two or three, and wherein the reaction is performed adiabatically in the nth reactor (the last reactor through which the reaction mixture to be hydrogenated flows).

The hydrogenation in step b) is preferably effected in n hydrogenation reactors connected in series, where n is preferably two or three, and wherein the nth reactor is operated in straight pass.

When the reaction mixture hydrogenated in one of the reactors connected downstream of the first reactor (i.e. in the 2nd to nth reactor) has only such low proportions of hydrogenatable fatty acid triglyceride that the exothermicity occurring in the reaction is insufficient to maintain the desired temperature in the reactor, heating of the reactor (or of individual reaction zones of the second reactor) may also be required. This can be effected analogously to the above-described removal of the heat of reaction by heating an external circulation stream or by internal heating. In a suitable embodiment, the temperature of a reactor can be controlled by using the heat of reaction from at least one of the upstream reactors.

In addition, the heat of reaction withdrawn from the reaction mixture can be used to heat the feed streams to the reactors. For instance, the fatty acid triglyceride feed stream into the first reactor can be mixed at least partly with an external circulation stream of this reactor and the combined streams can then be conducted into the first reactor. In addition, in the case of m=2 to n reactors, the feed stream from the (m−1)th reactor can be mixed in the mth reactor with a circulation stream of the mth reactor, and the combined streams can then be conducted into the mth reactor. In addition, the fatty acid triglyceride feed stream and/or another feed stream can be heated with the aid of a heat exchanger which is operated with heat of hydrogenation withdrawn.

In a specific embodiment of the process, a reactor cascade composed of n reactors connected in series is used, in which case the reaction is performed adiabatically in the nth reactor. In the context of the present invention, this term is used in the technical and not in the physicochemical sense. Thus, the reaction mixture generally experiences a temperature increase as it flows through the second reactor owing to the exothermic hydrogenation reaction. An adiabatic reaction is understood to mean a procedure in which the amount of heat released in the hydrogenation is absorbed by the reaction mixture in the reactor and no cooling by cooling apparatus is employed.

The heat of reaction is thus removed from the second reactor with the reaction mixture, apart from a residual content which is released from the reactor to the environment as a result of natural heat conduction and heat emission. The nth reactor is preferably operated in straight pass.

In a preferred embodiment, for the hydrogenation in step b), a two-stage reactor cascade is used, in which case the first hydrogenation reactor has a stream from the reaction zone conducted in an external circulation system. In a specific embodiment of the process, a reactor cascade composed of two reactors connected in series is used, in which case the reaction is performed adiabatically in the third reactor.

In a further preferred embodiment, for the hydrogenation in step b), a three-stage reactor cascade is used, in which case the first and second hydrogenation reactors have a stream from the reaction zone conducted in an external circulation system. In a specific embodiment of the process, a reactor cascade composed of three reactors connected in series is used, in which case the reaction is performed adiabatically in the third reactor.

In one embodiment, additional mixing can be effected in at least one of the reactors used. Additional mixing is especially advantageous when the hydrogenation is effected with long residence times of the reaction mixture. For the mixing, it is possible to use, for example, the streams introduced into the reactors, by introducing them into the particular reactors using suitable mixing devices, such as nozzles. For the mixing, it is also possible to use streams from the particular reactor conducted in an external circulation system.

To complete the hydrogenation, a discharge which still comprises hydrogenatable fatty acid triglyceride is withdrawn in each case from the first to (n−1)th reactor and is fed into the downstream hydrogenation reactor in each case. In a specific embodiment, the discharge is separated into a first and a second substream, in which case the first substream is fed back as a circulation stream to the reactor from which it has been withdrawn, and the second substream is fed to the downstream reactor. The discharge may comprise dissolved or gaseous fractions of hydrogen. In a specific embodiment, the discharge from the first to (n−1)th reactor is fed to a phase separation vessel and separated into a liquid phase and a gaseous phase, the liquid phase is separated into the first and the second substream, and the gas phase is fed separately at least partly to the downstream reactor. In an alternative embodiment, the discharge from the first to (n−1)th reactor is fed to a phase separation vessel and separated into a first liquid hydrogen-depleted substream and a second hydrogen-enriched substream. The first substream is then fed back as a circulation stream to the reactor from which it has been withdrawn, and the second substream is fed to the downstream reactor (as a fatty acid triglyceride- and hydrogen-containing feed). In a further alternative embodiment, the second to nth reactor is charged with hydrogen not via a hydrogenous feed withdrawn from the upstream reactor but rather with fresh hydrogen via a separate feed line.

The above-described process variant is particularly advantageously suitable for control of the reaction temperature and of the heat transfer between reaction medium, delimiting apparatus walls and environment. A further means of controlling the heat balance consists in regulating the entry temperature of the fatty acid triglyceride-containing feed. For instance, a lower temperature of the entering feed generally leads to improved removal of the heat of hydrogenation. When the catalyst activity declines, the entry temperature can be selected at a higher level in order to achieve a higher reaction rate and thus to compensate for the decline in catalyst activity. Advantageously, the service life of the catalyst used can thus generally be prolonged.

Step c)

At least one fatty alcohol-containing fraction is isolated (=step c) from the hydrogenation product obtained in step b).

In the simplest case, the hydrogenation discharge can be isolated as a fatty alcohol-containing fraction without subjecting it to a workup. This is the case when the remaining components present do not adversely affect the intended use.

In general, the hydrogenation discharge is subjected to a workup by customary methods known to those skilled in the art.

Suitable examples include thermal processes, preferably distillative processes, adsorption, ion exchange, membrane separation processes, crystallization, extraction or a combination of two or more of these processes. The hydrogenation discharge is preferably worked up by distillation. Suitable processes for this purpose are customary distillation processes known to those skilled in the art. Suitable apparatus for the distillative workup comprises distillation columns, such as tray columns, which may be provided with bubble-caps, sieve plates, sieve trays, packings, internals, valves, side draws, etc. Especially suitable are dividing wall columns, which may be provided with side draws, recycle lines, etc. For the distillation, it is possible to use a combination of two or more than two distillation columns. Also suitable are evaporators, such as thin-film evaporators, falling-film evaporators, Sambay evaporators, etc., and combinations thereof.

In a preferred embodiment of the process according to the invention, in step c), a stream comprising 1,2-propanediol is additionally isolated from the product of the hydrogenation.

The invention is illustrated in detail by the following, non-limiting examples.

EXAMPLES

Example 1

Continuous Hydrogenation of Rapeseed Oil Over a Fixed Bed Catalyst

The feed stream used was rapeseed oil which, after hydrolysis and analysis by means of GC/MS coupling, had the following fatty acid distribution:

| | |
|---|---|
| Palmitic acid | 4.5 area % |
| Stearic acid | 1.8 area % |
| Oleic acid | 66.0 area % |
| Linoleic acid | 24.2 area % |

This distribution gives rise to a maximum possible yield for the hydrogenation of 87% by weight of octadecanol and of 6.7% by weight of 1,2-propanediol.

To perform the hydrogenation process, a two-stage laboratory reactor cascade was used. The first reactor had a catalyst volume of 140 ml and the second reactor a catalyst volume of 100 ml. In both reactors, an oxidic material which comprises $CuO_{0.6-0.85}$ $(Al_2O_3)_{0.1-0.34}$ $(La_2O_3)_{0.01-0.2}$ was used as the catalyst (1st reactor: 182 g, 2nd reactor: 133 g). The catalyst was reduced in a hydrogen stream before the hydrogenation reaction.

The first reactor possessed a circulation system and was operated in trickle mode; the second reactor was operated in straight pass.

The continuous hydrogenation was effected over 1400 hours. The temperature in the first reactor was 205° C. at the reactor inlet and 220° C. at the reactor outlet; the temperature in the second reactor was a constant 200° C. The hydrogen pressure in both reactors was 200 bar. The catalyst hourly space velocity was set to 0.18 $kg_{rapeseed\ oil}/L_{cat} \times h$. No deactivation of the catalyst over the experimental period was detected.

Under the abovementioned conditions, a conversion of 97% and a yield of octadecanol of 85% by weight (98% of theory) were achieved.

The invention claimed is:

1. A process for preparing fatty alcohols comprising
   a) providing a stream comprising at least one fatty acid triglyceride,
   b) subjecting the stream comprising the fatty acid triglyceride to a hydrogenation in the presence of a catalyst, wherein said catalyst is an oxidic material consisting of copper, aluminum, and lanthanum, and said catalyst is used for said hydrogenation, and
   c) isolating at least one fatty alcohol-containing fraction from the hydrogenation product obtained in step b).

2. The process according to claim 1, wherein, in step a), a stream comprising at least one natural fat and/or at least one natural oil is provided.

3. The process according to claim 1, wherein the catalyst is an oxidic material of the composition $(CuO)_{0.6-0.8}$ $(Al_2O_3)_{0.1-0.34}$ $(La_2O_3)_{0.02-0.2}$.

4. The process according to claim 1, wherein the hydrogenation in step b) is effected at a temperature within a range from 100 to 320° C.

5. The process according to claim 1, wherein the hydrogenation in step b) is effected at a temperature within a range from 180 to 230° C.

6. The process according to claim 1, wherein the hydrogenation in step b) is effected at a pressure within a range from 100 to 325 bar.

7. The process according to claim 1, wherein the hydrogenation in step b) is effected at a pressure within a range from 180 to 230 bar.

8. The process according to claim 1, wherein the hydrogenation in step b) is continuous.

9. The process according to claim 1, wherein the hydrogenation in step b) is effected in n hydrogenation reactors connected in series, where n is an integer of at least two.

10. The process according to claim 9, where n is an integer of two or three.

11. The process according to claim 9, wherein the hydrogenation in step b) is effected in n hydrogenation reactors connected in series, where n is an integer of at least two, and the 1st to (n−1)th reactor possesses a stream from the reaction zone which is connected in an external circulation system.

12. The process according to claim 9, wherein the hydrogenation in step b) is effected in n hydrogenation reactors connected in series, where n is an integer of at least two, and wherein the reaction in the nth reactor is performed adiabatically.

13. The process according to claim 9, wherein the hydrogenation in step b) is effected in n hydrogenation reactors connected in series, where n is an integer of at least two, and wherein the nth reactor is operated in straight pass.

14. The process according to claim 9, wherein hydrogen is fed only into the first reactor.

15. The process according to claim 1, in which a stream comprising 1,2-propanediol is additionally isolated from the product of the hydrogenation in step c).

* * * * *